United States Patent [19]

De Vlieger et al.

[11] Patent Number: 5,807,566

[45] Date of Patent: Sep. 15, 1998

[54] COMPOSITION FOR CONTROLLING PESTS, PROCESS FOR THE PREPARATION THEREOF AND USE THEREOF IN CROP PROTECTION

[75] Inventors: Jan Jacobus De Vlieger, HP Delft; Peter Hans Smits, Wageningen, both of Netherlands

[73] Assignee: Nederlandse Organisatie voor Toegepast-Natuurwetenschappelijk Onderzoek, Delft, Netherlands

[21] Appl. No.: 507,414

[22] PCT Filed: Feb. 21, 1994

[86] PCT No.: PCT/NL94/00043

§ 371 Date: Oct. 4, 1995

§ 102(e) Date: Oct. 4, 1995

[87] PCT Pub. No.: WO94/18838

PCT Pub. Date: Sep. 1, 1994

[30] Foreign Application Priority Data

Feb. 24, 1993 [NL] Netherlands .............................. 9300345

[51] Int. Cl.⁶ .......................... A01N 25/10; A01N 25/14; A01N 25/22
[52] U.S. Cl. .......................... 424/409; 424/484; 424/486; 424/488; 424/499; 424/501
[58] Field of Search ..................................... 424/409, 484, 424/486, 488, 499, 501; 252/315.1, 315.3, 315.4

[56] References Cited

U.S. PATENT DOCUMENTS

| | | | |
|---|---|---|---|
| 4,331,652 | 5/1982 | Ludwig et al. | 424/486 |
| 4,798,786 | 1/1989 | Tice et al. | 435/177 |
| 4,844,896 | 7/1989 | Bohm et al. | 424/89 |
| 5,248,500 | 9/1993 | Ayanaba | 424/417 |
| 5,360,892 | 11/1994 | Bonsignore et al. | 424/497 |
| 5,523,293 | 6/1996 | Jane et al. | 514/21 |

FOREIGN PATENT DOCUMENTS

| | | |
|---|---|---|
| 2 317 882 | 2/1977 | France . |
| 82/00943 | 4/1982 | WIPO . |
| 89/04170 | 5/1989 | WIPO . |

OTHER PUBLICATIONS

Shapiro et al., Laboratory Evaluation of Dyes as Ultraviolet . . . , Journal of Economic Entomology, Feb. 1990, vol. 83, No. 1, pp. 168–172.

*Primary Examiner*—Edward J. Webman
*Attorney, Agent, or Firm*—Cushman Darby & Cushman IP Group of Pillsbury Madison & Sutro, LLP

[57] ABSTRACT

The present invention relates to compositions for controlling pests, such as insects, including an effective amount of a biological controlling agent, a degradable matrix, and a UV absorber. The UV absorber is bound to the degradable matrix, and preferably the absorber absorbs at a wavelength in the range of 280–400 nm. A cross-linking agent may be employed as well.

18 Claims, 2 Drawing Sheets

COMPOSITION FOR CONTROLLING PESTS, PROCESS FOR THE PREPARATION THEREOF AND USE THEREOF IN CROP PROTECTION

This application is a continuation under 35 U.S.C. 371 of PCT application NL 94/00043, filed Feb. 21, 1994.

BACKGROUND OF THE INVENTION

The invention relates to a composition for applying biological control agents such as viruses, bacteria, fungi and nematodes for controlling pests, the control agent being located in a matrix material in the presence of a UV absorber.

The control of insects and other pests using chemical means is facing increasing difficulties in connection with water and soil pollution, residues in food, resistance and inadequate specificity. The control of pests by biological means (viruses, bacteria, fungi and the like) has these drawbacks to a far lesser extent. Thus the bacterium *Bacillus thuringiensis* and certain baculoviruses are already being used successfully for controlling insects. A problem in spreading such agents is, however, that they must not only have a rapid lethal effect but also, as long as the pest has not been reached, must not be degraded or affected by atmospheric or environmental influences (sunlight, rain and the like). This requires that the biological agents (bacteria, viruses etc.) used for control should be incorporated in a material which, on the one hand, protects the agent against degradation and, on the other hand, releases the agent before or after ingestion by the plague organism.

Dutch Patent Application 78.09563 discloses an insecticide composition containing, as the control agent, for example the bacterium *Bacillus thuringiensis* which is embedded in small beads of protein and RNA, the purpose of the RNA being to absorb UV light (254 nm). RNA, however, is an expensive means of absorbing UV light and the small beads thus obtained are also insufficiently stable; furthermore, for the purpose of adequate protection, other (longer) wavelengths should also be absorbed.

The known compositions for biological pest control therefore provide insufficient protection, in particular against deterioration due to sunlight, so that the life of the compositions, particularly when used outside greenhouses, is inadequate, and larger quantities must be used than, strictly speaking, would be necessary. There is therefore great demand for long-acting, specific biological control agents, in particular for the treatment of crops which are grown in the open field.

SUMMARY OF THE INVENTION

Figure 1:
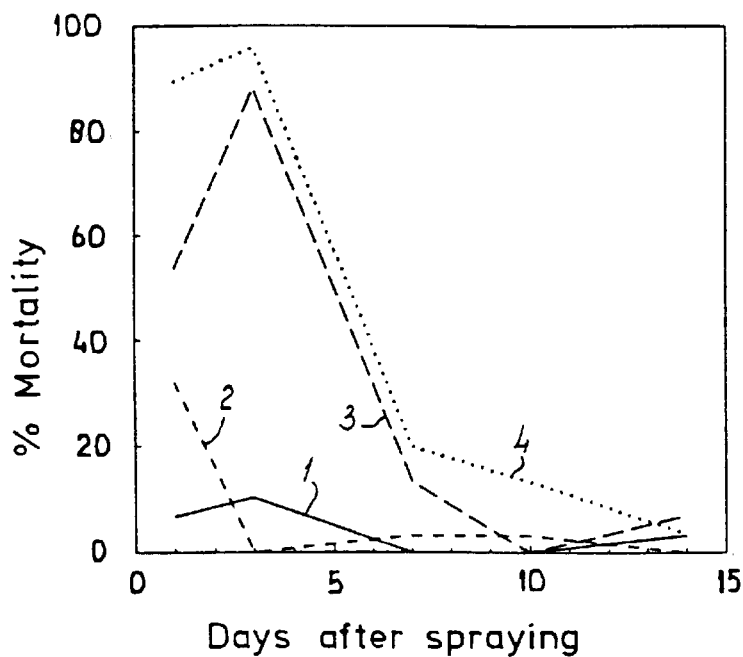
FIG. 1 shows the percentage mortality of *Sodoptera exigua* fed with leaf discs from bean plants sprayed with various virus formulations, after exposure to natural sunlight: (1): untreated control; (2) only SeNPV; (3): SeNPV in albumin; (4): SeNPV in albumin with CiB: (August).

A composition has now been found in which the biological agent is incorporated in a degradable matrix in the presence of a UV absorber in such a way that it is protected on a long-term basis against sunlight and other environmental influences and is therefore available on a long-term basis for effective biological control. A further advantage of the composition found is that it adheres effectively to leaves and as a result is not readily removed by rain or other weather effects.

DETAILED DESCRIPTION OF THE INVENTION

The composition according to the invention is characterized in that the UV absorber is bound to the matrix material. The UV absorber is preferably bound covalently (chemically) to the matrix material. The amount of UV absorber used may vary from, for example, 1 to 125% by weight, more particularly from 5 to 100% by weight based on the matrix material.

The degradable matrix material for the composition according to the invention may, for example, be a protein, a polysaccharide such as cellulose, starch, alginate or lignin or fractions or derivatives or mixtures thereof, or a synthetically prepared or modified degradable polymer such as a polyester, for example a homo- or copolymer of dilactide or lactic acid, or a polyamide. The term degradable means chemically or enzymatically degradable in or by the organisms to be controlled, preferably in the stomach or foregut (pH 9–10) of insects, within a period in which the biological control agent can be released, for example an hour or a few hours. In the case of viruses, the matrix should be degraded sufficiently for binding to the gut epithelium of the pest.

The matrix material preferably contains functional groups such as hydroxyl, carboxyl, amino or thiol groups, by means of which the matrix may be cross-linked.

The matrix material may, in particular, be a protein. The protein should contain functional groups such as free amine, hydroxyl and/or thiol groups, i.e. it should for example contain arginine, cysteine, histidine, lysine, ornithine, serine, tyrosine and/or threonine units. Preferably, the protein contains free amine groups, as in lysine. A protein which was found to be suitable is albumin, for example bovine serum albumin.

The protein has preferably been gelled with a crosslinking agent. In this context, a crosslinking agent refers to a compound which, by physical or chemical interaction, brings about a coupling between two amino acid chains.

An example of chemical interaction between amino acid chains via a crosslinking agent is the reaction of a dialdehyde such as glutar-aldehyde or an acetal thereof with a free protein amine group, for example of lysine, resulting in imine coupling groups.

Another example is the reaction of a dithiol with protein thiol groups (possibly formed after reduction of disulphide bridges), for example of cysteine, resulting in disulphide or other coupling groups.

Other coupling agents, such as mercaptoalcohols (in particular mercaptoalkanols), diketones (for example butanedione), diacyl halides (for example terephthaloyl dichloride), diimides (for example 1-ethyl-3-(3- dimethylaminopropyl)carbodiimide), bis-succinimidyl esters and the like can also be used to bring about crosslinking.

Dithiols and mercaptoalcohols are found to be particularly useful as crosslinking agents. Examples of suitable dithiols are alkanedithiols and hydroxyalkanedithiols such as dithioglycerol, dithioerythritol and dithiothreitol. Examples of suitable mercaptoalcohols are mercaptoethanol (thioglycol) and mercaptopropanediol (monothioglycerol).

The agents and reactions reported hereinbefore for gelling proteins can also be applied to other matrix materials such as poly-saccharides which are likewise very suitable for the compositions according to the invention. Other suitable matrix materials are poly-carboxylic acids such as polyacrylate or alginate, and polyesters such as polylactate.

Bonding between the UV absorber and the matrix material can be achieved as a result of the UV absorber being a so-called reactive dye, i.e. a compound containing reactive sites. A reactive site is, for example, a halogen atom which is susceptible to nucleophilic substitution, or an activated double bond such as a vinyl sulphone which is susceptible to nucleophilic addition. The substitution or addition can be effected by, for example, a free amine group, hydroxyl group or thiol group of the matrix material with the formation of a covalent bond between the dye and a matrix molecule. Dyes having such a reactive site are, for example, triazinyl dyes containing reactive halogen, such as monochloro- and dichlorotriazinyl dyes (for coupling thereof see Böhme et al., *J. Chromatogr.* 69, 209 (1972)). Other possible reactive dyes are those which contain a vinylsulphonyl group. Such coupling reactions are depicted schematically below. Here, Mat represents the matrix material, and Abs represents the UV absorber.

Mat-NH$_2$+Cl-Abs→Mat-NH-Abs

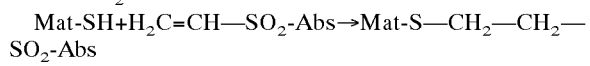
Mat-SH+H$_2$C=CH—SO$_2$-Abs→Mat-S—CH$_2$—CH$_2$—SO$_2$-Abs

Suitable examples of reactive triazinyl dyes are Cibacron Brilliant Yellow 3G-P (Reactive Yellow 2; Color Index 18972; CiY) and Cibacron Blue F3G-A (Reactive Blue 2; Color Index 61211; CiB). The UV absorber preferably absorbs radiation in the near UV, i.e. having a wavelength of 280–400 nm, in particular radiation in the range of 280–320 nm.

A different type of coupling is possible if the UV absorber contains a free amino group, as in amido-G acid (7-amino-1,3-naphthalenedicarboxylic acid). An absorber of this type can be coupled, for example with the aid of a carbodiimide according to the scheme below, 100% to an alginate (cf. Prouchayret et al., *Pol. Bull.* 21, 309 (1989)).

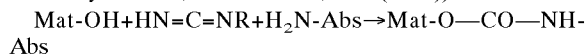
Mat-OH+HN=C=NR+H$_2$N-Abs→Mat-O—CO—NH-Abs

Yet a further possibility is the coupling of amine-containing absorbers, such as amido-G acid, to oxidized polysaccharides (glucans), which contain aldehyde groups, followed by reduction of the imine formed in the first instance according to the scheme below (cf. Schacht et al., *J. Contr. Rel.,* 1, 33 (1984)).

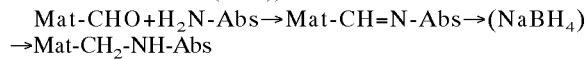
Mat-CHO+H$_2$N-Abs→Mat-CH=N-Abs→(NaBH$_4$)→Mat-CH$_2$-NH-Abs

These and other known principles for coupling an absorber to a matrix material may be varied in a manner known to those skilled in the art, depending on the type of the materials.

The control agent of the composition according to the invention may be of various kinds. In general, it involves agents which are sensitive to degradation as a result of environmental influences, in particular of sunlight. The control agent is, in particular, an agent for the biological control of pests such as insects. This includes viruses, in particular baculoviruses, the most important group being the nuclear polyhedrosis viruses (NPV). Examples of these are *Heliothis zea* NPV (HzNPV), *Lymantria dispar* NPV (LdNPV), *Cydia pomonella* NPV (CpNPV) and *Spodoptera exigua* NPV (SeNPV). The viruses may be of the natural type or may have been modified genetically.

This further includes bacteria such as *Bacillus thuringiensis, B. popillia* and *B. sphearicus*, rickettsias, protozoa, fungi such as *Beauveria bassiana* and *Verticillium lecanii* and nematodes (eelworms), for example of the genera Neoaplectana, Steinernema and Heterorhabditis. Biological control of insects and other pests by means of viruses, bacteria and the like is known per se (see, for example, P. H. Smits, "Microbial Control of Insect Pests", in "Modern Crop Protection; Developments and Perspectives": p. 189–198, Ed. J. C. Zadoks, Wageningen Press 1993).

The concentration of the control agent in the composition can be selected according to the application. In general, from 1 to $10^{12}$ particles (virus particles, bacterial and fungal spores and the like), for example from $10^3$ to $10^{11}$ particles, preferably from $10^7$ to $10^{10}$ particles per g of carrier material (protein) can be used. With respect to the carrier material, the composition preferably contains from 0.001 to 10% by weight, in particular approximately from 0.1 to 1% by weight of biological material.

The composition may also contain further components such as preservatives, attractants, coatings, moisture repellants and the like. For the purpose of spraying, the composition can be used as such (dry) or as a suspension or solution in a suitable solvent such as water. A suitable concentration of a solution or a suspension is, for example, 1 kg of dry composition per 10–2000 l of solvent.

The invention also relates to a process for preparing a composition as described hereinabove, according to which a matrix material is brought into contact with a reactive dye, and the matrix material is cross-linked, at least in part, in the presence of a biological control agent. The process according to the invention has the advantage that it can be carried out under mild conditions, so that a well-encapsulated and protected, yet at the same time still completely active biological control agent is obtained. The process can be carried out, if required, at temperatures below 37° C. which is necessary, for example, in the case of fungal spores as these would otherwise not survive the treatment. In the case of *B. thuringiensis*, for example, a spore can withstand a higher temperature (70° C.) for some time, but a crystal can not.

The steps of the process can be carried out simultaneously. This involves bringing together matrix material, UV absorber (dye), control agent and cross-linking agent under suitable conditions, for example in a buffered aqueous medium. Alternatively, the UV absorber can first be coupled to the matrix material, whereupon the biological control agent and the cross-linking agent are added and the mixture is cross-linked.

Coupling of the dye with the matrix material preferably proceeds directly by displacing a reactive group of the dye by a functional group of the protein. If necessary, a coupling agent may also be used which brings about a bond, on the one hand, with the dye and, on the other hand, with the matrix material. After the UV absorber has been coupled to the matrix material, any excess of absorber is preferably removed, for example by Soxhlet extraction or filtration.

The matrix material used is preferably a protein. The protein material can be made to gel after the protein has been brought into contact with a dye, or at the same time. The protein material may, in the presence of the microorganism to be used for control, be gelled by means of a crosslinking agent such as a dithiol, as described hereinbefore. The amount of crosslinking agent may vary, depending on the type of aid, the loading of the protein with microorganisms and the desired mechanical strength of the gel. For example, 1–30% by weight, more particularly approximately 3–20% by weight of crosslinking agent is used, based on the protein material.

The product of the process according to the invention is preferably freeze-dried.

The invention further relates to a method for controlling pests such as insects, with the aid of the compositions described hereinbefore. This involves applying the composition, in a suitable form (powders, granules, suspensions and the like) and in a suitable dose, for example to the crop to be protected. A suitable dose is, for example, an amount of from 100 g to 10 kg per ha.

EXAMPLE I

Virus SeNPV (42 mg, $1.4 \times 10^{10}$ polyhedra per g), suspended in phosphate buffer (pH about 7), is vibrated ultrasonically for 30 minutes in a vibrating bath. This is then admixed successively with 4 g of albumin in 12 g of phosphate buffer, 226 mg of dithiothreitol in 2.7 g of phosphate buffer (pH 6.7) and 3.2 g of Cibacron Blue. After cross-linking, the gel is washed with water until the wash water is no longer coloured, and is then freeze-dried, ground and screened.

EXAMPLE II 10 ml (12.6 g) of 0.1475 mM KOH in methanol is admixed with 1.0 g of Cibacron Yellow and 1.28 g of albumin. After 24 hours at room temperature, the product is extracted with 250 ml of methanol. The extracted coupling product, evaporated to dryness, is admixed with virus solution ($10^9$ SeNPV polyhedra per ml of phosphate buffer, pH=6.7) in such an amount that $3 \times 10^9$ virus particles per g of coupling product are present. Four times the weight, compared to the amount of coupling product, of phosphate buffer and 0.1 times that amount of dithiothreitol are then added, whereupon crosslinking takes place over 24 hours. The gel is then freeze-dried, ground and screened.

EXAMPLE III

Freeze-dried virus SeNPV ($4 \times 10^8$ PIBs/mg) was formulated in albumin with or without Cibacron Blue (CiB) (1% of virus, 19% of CiB by weight based on albumin) according to the procedure of Example I. All the samples were applied to a slide which was placed on a cooled plate and irradiated with a UV lamp (HPA-2000, Philips) for from 0 to 480 minutes at a distance of 35 cm. The virus, formulated or not formulated, was then rinsed off the slides again and resuspended in phosphate buffer (PBS). These suspensions were applied, using a pipette, to lettuce leaf discs (diameter 11 mm) in a concentration of 2000 polyhedra in 10 µl of buffer per disc. The discs were placed in wells of culture tissue plates which had been filled with a layer of 1.5% of aqueous agar. To each well, third-stage beet army worm (*Spodoptera exigua*) was added. The plates were stored in the dark at 25° C. After 1 to 2 days, for each concentration, 30 caterpillars which had eaten all of the leaf disc were transferred into the wells of 12-well bioassay plates in which caterpillar feed had been smeared. After 7 days at 25° C., the mortality was determined. The experiment was carried out twice, using different light exposure times. Tables A and B show the results of the two experiments.

TABLE A

Percentage mortality of *Spodoptera exigua* fed with irradiated virus formulations.

| Irradiation: | 0 min | 4 min | 16 min | 64 min | 256 min |
|---|---|---|---|---|---|
| PBS buffer | 0 | — | — | — | — |
| Unformulated virus | 57 | 40 | 10 | 7 | 3 |
| Virus in albumin | 100 | 37 | 7 | 3 | 0 |
| Virus in albumin + Cibacron Blue | 80 | 100 | 93 | 83 | 87 |

TABLE B

Percentage mortality of *Spodoptera exigua* fed with irradiated virus formulations.

| Irradiation: | 0 hour | 1 hour | 2 hours | 4 hours | 8 hours |
|---|---|---|---|---|---|
| PBS buffer | 0 | | | | |
| Unformulated virus | 16.7 | 6.7 | 0 | 0 | 0 |
| Virus in albumin + Cibacron Blue | 56.7 | 60.0 | 73.3 | 55.2 | 60.0 |

Conclusion: Cibacron Blue, added to virus encapsulated in albumin, protects the virus for at least 8 hours against the degrading effect of UV radiation from a HPA-2000 lamp. Albumin on its own provides the virus with only limited or no additional protection.

EXAMPLE IV

Bean plants in trays (30×40 cm) were sprayed, with the aid of a compressor and a test tube atomiser, with SeNPV virus suspensions in various formulations. The dose used was $1.5 \times 10^7$ PIBs/11 ml of water (incl. 0.025% citowett). The formulations consisted of unformulated freeze-dried virus in PBS, freeze-dried virus formulated in crosslinked albumin (1% by weight) and the same virus/albumin formulation to which Cibacron Yellow (CiY) 6% and 42% by weight, based on albumin, or Cibacron Blue (CiB) 14%, 19% and 39% by weight had been added. The plants were exposed outside to natural sunlight. On days 0, 4, 7, 11 and 14, discs (diameter 11 mm) were cut out of the bean plants sprayed on day 0 and were fed to third-stage beet army worms as described in Example III. After 8 days the mortality was determined.

FIG. 1 shows the percentage mortality of *Spodoptera exigua* fed with leaf discs from bean plants sprayed with various virus formulations, after exposure to natural sunlight; (1): untreated control; (2) only SeNPV; (3): SeNPV in albumin; (4): SeNPV in albumin with CiB; (August).

Figure 2:
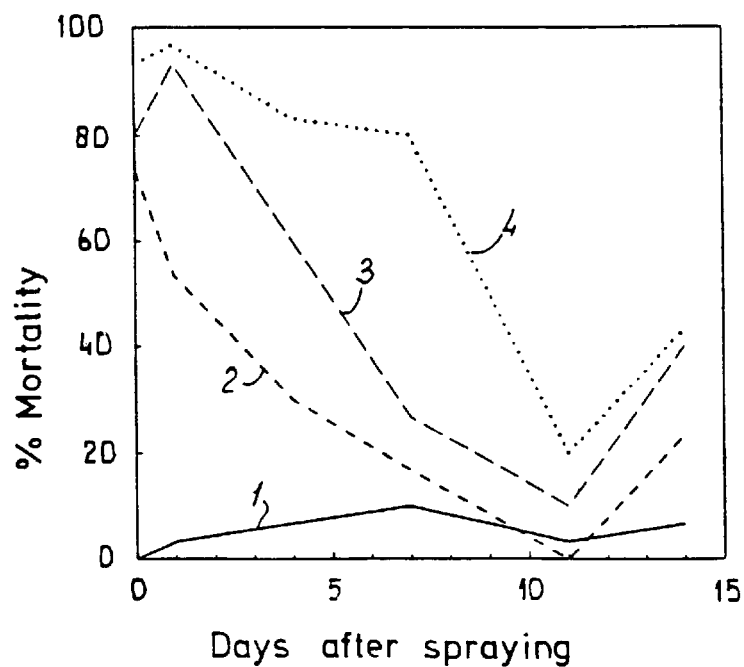
FIG. 2 shows the percentage mortality of *Sodoptera exigua* fed with leaf discs from bean plants sprayed with various virus formulations, after exposure to natural sunlight; (1): untreated control; (2) only SeNPV; (3): SeNPV in albumin; (4): SeNPV in albumin with CiB; (October).

FIG. 2 shows the percentage mortality of *Spodoptera exigua* fed with leaf discs from bean plants sprayed with various virus formulations, after exposure to natural sunlight; (1): untreated control; (2) only SeNPV; (3): SeNPV in albumin; (4): SeNPV in albumin with CiB; (October).

Figure 3:
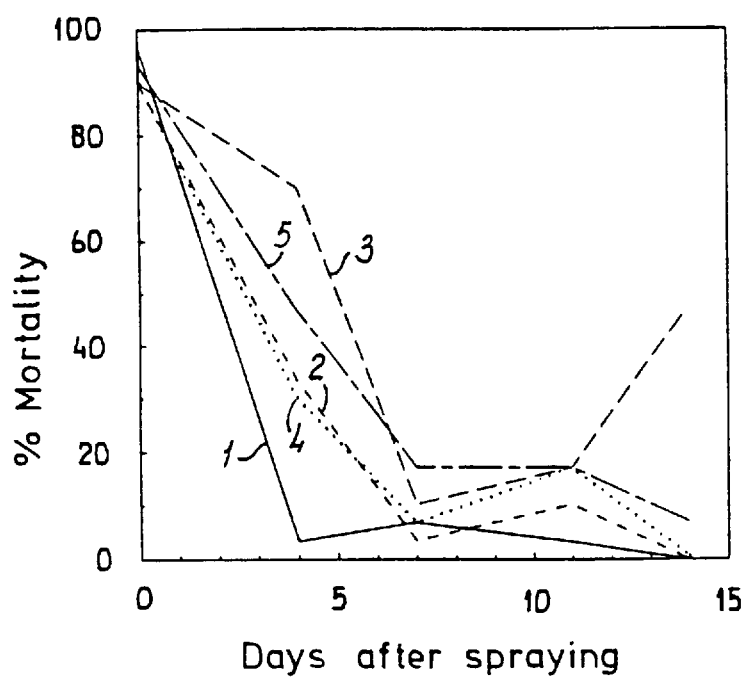
FIG. 3 shows the percentage mortality of *Sodoptera exigua* fed with leaf discs from bean plants sprayed with various virus formulations, after exposure to natural sunlight; (1): only SeNPV; (2): SeNPV in albumin with 42% CiY; (3): SeNPV in albumin with 6% CiY; (4): SeNPV in albumin with 39% CiB; (5): SeNPV in albumin with 14% CiB; (July).

FIG. 3 shows the percentage mortality of *Spodoptera exigua* fed with leaf discs from bean plants sprayed with various virus formulations, after exposure to natural sunlight; (1): only SeNPV; (2): SeNPV in albumin with 42% CiY; (3): SeNPV in albumin with 6% CiY; (4): SeNPV in albumin with 39% CiB; (5): SeNPV in albumin with 14% CiB; (July).

Conclusion: The addition both of Cibacron Blue and of Cibacron Yellow has a protective effect on the degradation of the virus by UV irradiation. The effect is greater in the autumn than in summer.

EXAMPLE V

Trays (30×40 cm) with 12 bean plants were treated with virus formulated in albumin (1% by weight) with CiB (14% by weight) or CiY (6% by weight), as described in Example IV. In this case, however, one tray of each treatment, after having been sprayed with virus and dried for 2 hours, was sprinkled, via a sprinkler head, with tap water to a volume of 10 liters (Experiment 1) and 20 liters (Experiment 2) per square meter, comparable to a substantial shower of rain. After drying again for 2 hours, the experiment was further carried out as described in Example IV for day 0. The results are shown in Table C.

TABLE C

Percentage mortality of *Spodoptera exigua* fed with irradiated leaf discs, sprinkled or not sprinkled with 10 l/m$^2$ and 20 l/m$^2$, respectively, and containing virus formulations.

|  | without sprinkling | | with sprinkling | |
| --- | --- | --- | --- | --- |
|  | Experiment 1 | Experiment 2 | Experiment 1 | Experiment 2 |
| PBS | 0 | 3.3 | — | — |
| Unformulated virus | 96.7 | 93.3 | 96.7 | 93.3 |
| Virus in albumin + Cibacron Blue | 100 | 93.3 | 93.3 | 86.7 |
| Virus in albumin + Cibacron Yellow | 96.7 | 80.8 | 96.7 | 73.3 |

Conclusion: The formulated product adheres sufficiently to the plant surface, no reduction in efficacy takes place as a result of sprinkling.

We claim:

1. Composition for controlling pests comprising an effective amount of a biological pest controlling agent, a degradable polymeric matrix and a UV absorber, wherein the UV absorber is covalently bound to the polymeric matrix and the agent is incorporated in the polymeric matrix.

2. The composition according to claim 1, wherein the UV absorber is derived from a reactive, chlorine-containing triazinyl dye or from a dye containing a vinylsulphonyl group.

3. The composition according to claim 1, wherein the UV absorber absorbs at a wavelength in the range of 280–400 nm.

4. The composition according to claim 1, wherein the degradable matrix is a protein, a polysaccharide or polyester.

5. The composition according to claim 4, wherein the degradable matrix is a protein.

6. The composition according to claim 5, wherein the protein is cross-linked with a cross-linking agent.

7. The composition according to claim 6, wherein the cross-linking agent is a dithiol or a mercapto-alcohol.

8. Method for preparing a composition according to claim 1, wherein a degradable polymeric matrix material is brought into contact with a reactive UV absorber which absorbs at a wavelength in the range of 280–400 nm and cross-links the polymeric matrix material at least in part, in the presence of a microorganism.

9. The method according to claim 8, wherein the matrix material is a protein and the protein material is cross-linked by means of a cross-linking agent.

10. The method according to claim 9, wherein the polymeric protein material is cross-linked during or after contact with the UV absorber.

11. Method for controlling pests comprising the step of applying to pests or areas suspected of having pests the composition according to claim 1.

12. The composition of claim 3, wherein the UV absorber absorbs at a wavelength in the range of 280–320 nm.

13. The composition of claim 4, wherein the polyester is a polylactate.

14. The composition of claim 1, wherein the biological pest controlling agent is a microorganism.

15. The composition of claim 14, wherein the microorganism is a nematode, a virus or a bacteria.

16. The composition of claim 6, wherein the cross-linking agent is selected from the group consisting of a dithiol, a mercapto-alcohol, a dialdehyde, a diketone, a diacyl halide and a diimide.

17. The method according to claim 9, wherein the cross-linking agent is a dithiol or a mercapto-alcohol.

18. The method according to claim 11, wherein the pests are insects.

* * * * *